United States Patent
Blom

(10) Patent No.: US 6,436,121 B1
(45) Date of Patent: Aug. 20, 2002

(54) REMOVABLE BLOOD FILTER

(76) Inventor: Paul H. Blom, 5812 Fifth Ave. M-12, Pittsburgh, PA (US) 15232

( * ) Notice: Subject to any disclaimer, the term of this patent is extended or adjusted under 35 U.S.C. 154(b) by 0 days.

(21) Appl. No.: 09/846,825

(22) Filed: Apr. 30, 2001

(51) Int. Cl.⁷ .............................................. A61M 29/00
(52) U.S. Cl. ..................................................... 606/200
(58) Field of Search .............................. 606/200, 151, 606/154, 157, 127

(56) References Cited

U.S. PATENT DOCUMENTS

| | | |
|---|---|---|
| 4,425,908 A | 1/1984 | Simon |
| 4,619,246 A | 10/1986 | Molgaard-Nielsen et al. |
| 4,643,184 A | 2/1987 | Mobin-Uddin |
| 4,990,156 A | 2/1991 | Lefebvre |
| 5,133,733 A | 7/1992 | Rasmussen et al. |
| 5,234,458 A | 8/1993 | Metais |
| 5,329,942 A | 7/1994 | Gunther et al. |
| 5,344,427 A | 9/1994 | Cottenceau et al. |
| 5,354,310 A | 10/1994 | Garnic et al. |
| 5,383,887 A | 1/1995 | Nadal |
| 5,415,630 A | 5/1995 | Gory et al. |
| 5,549,626 A | 8/1996 | Miller et al. |
| 5,649,906 A | 7/1997 | Gory et al. |
| 5,669,933 A | 9/1997 | Simon et al. |
| 5,695,518 A | 12/1997 | Laerum |
| 5,720,764 A | 2/1998 | Naderlinger |
| 5,725,550 A | 3/1998 | Nadal |
| 5,800,457 A | 9/1998 | Gelbfish |
| 5,800,525 A | 9/1998 | Bachinski et al. |
| 5,836,868 A * | 11/1998 | Ressemann et al. |
| 5,836,968 A | 11/1998 | Simon et al. |
| 5,848,964 A | 12/1998 | Samuels |
| 5,893,869 A | 4/1999 | Barnhart et al. |
| 5,954,745 A | 9/1999 | Gertler et al. |
| 5,968,071 A | 10/1999 | Chevillon et al. |
| 5,976,172 A | 11/1999 | Homsma et al. |
| 6,007,558 A | 12/1999 | Ravenscroft et al. |
| 6,027,520 A * | 2/2000 | Tsugita et al. ............... 606/200 |
| 6,066,149 A * | 5/2000 | Samson et al. |
| 6,080,178 A | 6/2000 | Meglin |

* cited by examiner

Primary Examiner—Ismael Izaguirre
(74) Attorney, Agent, or Firm—Thorp Reed & Armstrong LLP

(57) ABSTRACT

The present invention provides a blood filter comprising a plurality of central struts, the distal ends thereof intersecting at a vertex, a hollow tubular member having distal and proximal ends in fluid communication, and having at least one vertical strut extending therefrom, and means for retaining the plurality of central struts within the hollow tubular member. At least the outer layer of the hollow tubular member is made of a flexible material which resists the ingrowth of tissue around the central struts of the filter. The blood filter of the present invention can reduce the occurrence of circulatory occlusions, including pulmonary embolism, in patients and because of the hollow tubular member being made from a material which resists the ingrowth of tissue, it can easily be removed from the venous system of the patient when there is no longer an indication for its use.

48 Claims, 7 Drawing Sheets

REMOVABLE BLOOD FILTER

FIELD OF THE INVENTION

The present invention relates in general to blood filtration, and more specifically to a blood filter that is removable.

BACKGROUND OF THE INVENTION

Deep vein thrombosis is a condition in which a blood clot, called a thrombus, develops in the vein of a patient. The thrombus or a portion of it may break off, in which case it is called an embolus, travel through the venous system and become lodged in the patient's heart or lungs. Emboli lodged in the lungs, a condition termed pulmonary embolism, are potentially dangerous because the emboli may obstruct the arteries of the lung and lead to death.

It is estimated that deep vein thrombosis afflicts approximately 200,000 people every year. Deep vein thrombosis and pulmonary embolism most often occur in bedridden patients, but may also occur in ambulatory or otherwise healthy people. Deep vein thrombosis is a major complication for orthopedic surgical patients, such as those who have undergone major hip or knee surgery and for patients suffering from cancer or other chronic illnesses.

One study estimated that 600,000 people develop pulmonary emboli each year and it proves fatal for 90,000 of them. (See, *Vascular Surgery Principles and Practice*, Samuel Wilson, et al., Ch. 59, $3^{rd}$ Ed. 1996). Patients suffering from deep vein thrombosis and/or pulmonary embolism are typically treated with an initial course of intravenous anticoagulant, such as heparin, followed by a course of oral anticoagulant to try to dissolve the thrombi and/or emboli. However, anticoagulant therapy may not always be completely effective for some patients, and may be contraindicated in other patients, so that for those patients other measures must be employed.

A common treatment option for patients with deep vein thrombosis and/or pulmonary embolism, where anticoagulant therapy has not been completely effective or is contraindicated, is the surgical insertion of a blood filter into a large blood vessel such as the vena cava. The inferior vena cava is a large vein that empties blood into the heart received from the legs and lower abdominal area. The superior vena cava is a large vein that empties blood into the heart received from the head, neck, arms and chest. Vena cava filters can prevent emboli from entering the patient's heart and lungs by filtering the blood before it returns to the heart. Some vena cava filters are permanently implanted in the patient and remain with them for life. Some newer vena cava filters can be removed if there is no longer an indication for their use.

A significant drawback associated with the use of a removable vena cava filter is that the longer the filter remains in the patient, the greater the chance of tissue growth into and around the filter. This ingrowth can result in blockages forming in the blood vessel at the site of the filter. Such blockages can narrow or occlude the vessel at the region of the filter. Another problem associated with tissue ingrowth is that removal of the vena cava filter can be complicated because the blood vessel may rip or tear as the surgeon attempts to remove the filter that is ingrown with tissue. This problem may be especially pronounced in children treated by vena cava filter implantation, because children are growing and therefore may be more likely to experience rapid tissue ingrowth. Removable vena cava filters have heretofore neglected the problem of tissue ingrowth.

Therefore, a need exists in the art for a blood filter which will be removable and which will resist or prevent the ingrowth of tissue thereby facilitating easier removal from the blood vessel.

SUMMARY OF THE INVENTION

The present invention provides such a blood filter, which can reduce the occurrence of circulatory occlusions, including pulmonary emboli, in patients and can easily be removed from the venous system of the patient where there is no longer an indication for its use.

The present invention provides a blood filter comprising a plurality of central struts, the distal ends thereof intersecting at a vertex, a hollow tubular member having distal and proximal ends in fluid communication, and having at least one vertical strut extending therefrom, and means for retaining the plurality of central struts within the hollow tubular member.

The present invention further provides a blood filter comprising a plurality of central struts, the distal ends thereof intersecting at a vertex, and a hollow tubular member having distal and proximal ends in fluid communication, with at least one vertical strut extending therefrom, wherein the plurality of central struts are retained within the hollow tubular member.

The present invention yet further provides a method of using a blood filter to reduce circulatory occlusion in a patient, the blood filter comprising a plurality of central struts, the distal ends thereof intersecting at a vertex and a hollow tubular member having distal and proximal ends in fluid communication, with at least one vertical strut extending therefrom, wherein the plurality of central struts are retained within the hollow tubular member, the method comprising, surgically implanting the blood filter into a blood vessel of the patient such that the hollow tubular member lies adjacent to the inner wall of the blood vessel and such that blood flows through the filter The present invention still further provides a method of using a blood filter to reduce circulatory occlusion in a patient, the blood filter comprising a plurality of central struts, the distal ends thereof intersecting at a vertex, a hollow tubular member having distal and proximal ends in fluid communication, and having at least one vertical strut extending therefrom, and means for retaining the plurality of central struts within the hollow tubular member, the method comprising, surgically implanting the blood filter into a blood vessel of the patient such that the hollow tubular member lies adjacent to the inner wall of the blood vessel and such that blood flows through the filter.

The present invention also provides a method of using at least one blood filter to reduce circulatory occlusion in a patient, the at least one blood filter comprising a plurality of central struts, the distal ends thereof intersecting at a vertex, a hollow tubular member having distal and proximal ends in fluid communication with at least one vertical strut extending therefrom, and a means for retaining the plurality of central struts within the hollow tubular member, the method comprising, surgically implanting at least one blood filter into at least one blood vessel of the patient such that blood flows through the at least one blood filter and such that the hollow tubular member lies adjacent to the wall of the at least one blood vessel.

These and other advantages and benefits of the present invention will be apparent from the Detailed Description of the Invention herein below.

BRIEF DESCRIPTION OF THE FIGURES

The present invention will now be described for the purpose of illustration and not limitation in conjunction with the following figures wherein.

DETAILED DESCRIPTION OF THE INVENTION

The term "patient" generally refers to living humans and/or animals in which the blood filter of the present invention may be employed, but may also include cadavers used for training and/or teaching purposes.

In the following detailed description, the terms "distal" and "proximal" will be used. As used herein, the term "proximal" refers to that region, portion or end of a device or procedure nearest the person using the device or performing the procedure, while the term "distal" refers to that region, portion or end of a device or procedure nearest a patient upon whom the device is being used or the procedure is being performed.

Figure 1:
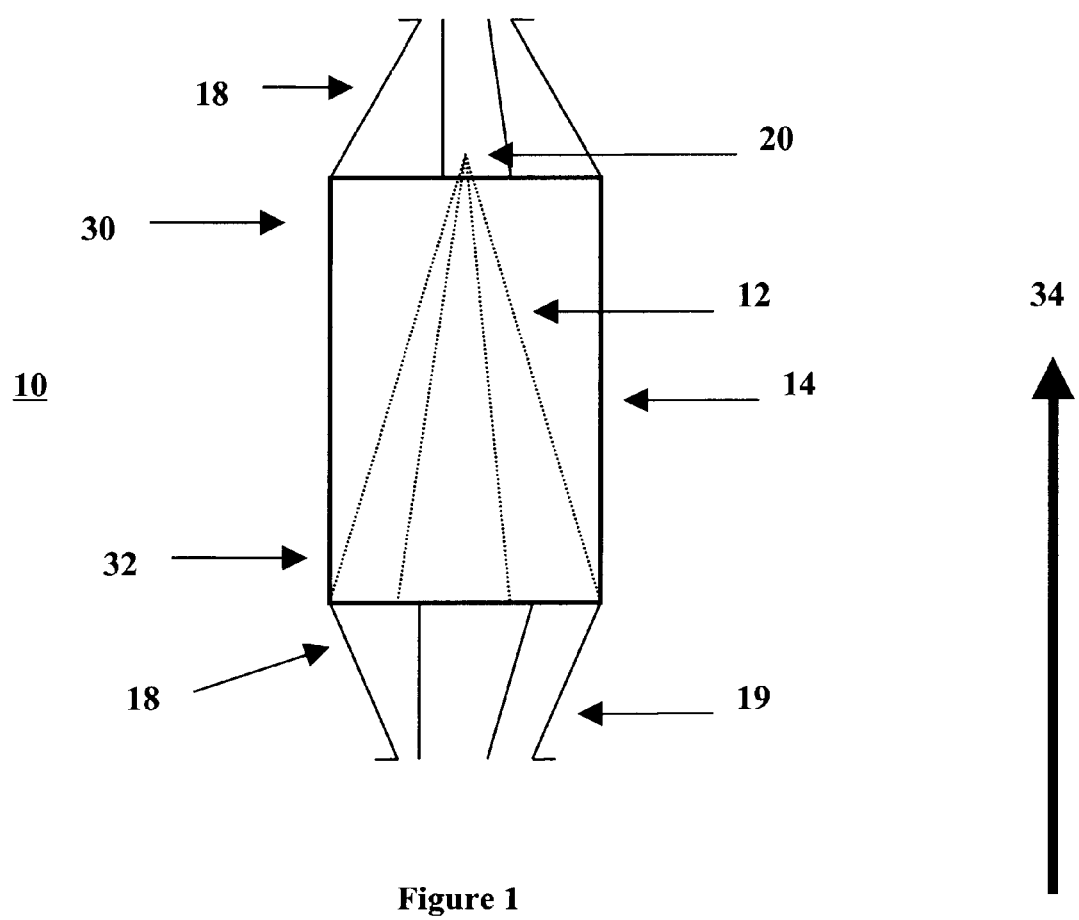
FIG. 1 illustrates the blood filter of the present invention.

The blood filter of the present invention is illustrated in FIG. 1. It comprises a plurality of central struts, 12 the distal ends thereof intersecting at a vertex 20. The plurality of central struts 12 is retained within a hollow tubular member 14 by a retaining means discussed below. The hollow tubular member 14 has a distal end 30 and a proximal end 32 in fluid communication. The hollow tubular member 14 has at least one vertical strut 18 extending therefrom. Preferably, the hollow tubular member has a plurality of vertical struts extending therefrom. The blood filter of the present invention may be deployed with the plurality of central struts in either an expanded or unexpanded state. Although depicted herein as conical, in an expanded state the plurality of central struts 12 may take a variety of forms including but not limited to, umbrella and basket-shaped. The preferred direction of blood flow through the blood filter of the present invention as indicated by arrow 34 is from proximal end 32 to distal end 30.

Figure 2:
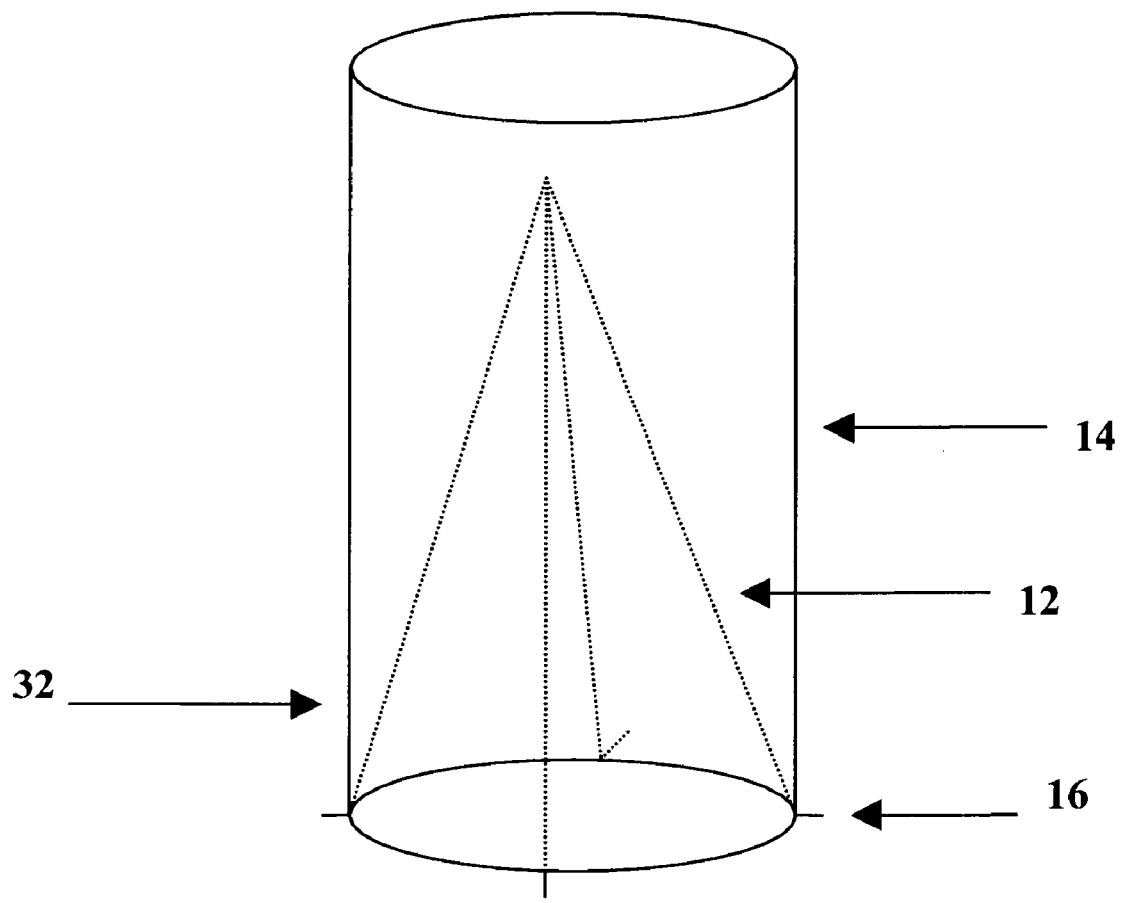
FIG. 2 illustrates a retaining means comprising feet on the ends of the plurality of central struts engaging the hollow tubular member of the present invention.

The inventor contemplates a number of possible means for retaining the plurality of central struts within the hollow tubular member. For example, the retaining means may comprise the plurality of central struts 12 exerting a self-expanding radial force on the surface of the inner wall of the hollow tubular member 14 to provide friction between the central struts and the wall. In another form, as illustrated in FIG. 2, the retaining means can comprise the plurality of central struts 12 having appendages 16 on the proximal ends thereof and the appendages engaging the proximal end 32 of hollow tubular member 14. The retaining means may also comprise some of the proximal portion of each strut of the plurality of central struts being embedded within the wall of hollow tubular member during manufacture of the filter.

At least the outer layer of the hollow tubular member 14 can be made of a flexible, biocompatible material that impedes ingrowth of tissue around the central struts of the filter, although the inventor prefers that the entire hollow tubular member 14 be made of such a material. Examples of such flexible, biocompatible, ingrowth-resistant materials include, but are not limited to: low density polyethylene; high density polyethylene; polyesters made from polyethylene terephthalate such as those sold under the name Dacron®; polypropylene; polystyrene; polycarbonate; and fluorinated ethylene propylene and tetrafluoroethylene polymers marketed under the Teflon® name. A particularly preferred material in this regard is polytetrafluoroethylene, including expanded polytetrafluoroethylenes commercially available under the Gore-Tex® name.

Referring again to FIG. 1, the vertical strut(s) 18 may preferably have at least one unidirectional hook 19 thereon to assist in recapture and removal of the blood filter of the present invention. The central struts 12 and vertical struts 18 of the blood filter 10 of the present invention preferably can be made of a material that will allow the struts to collapse into a delivery and retrieval device, such as a catheter, and that will allow the struts to expand to assume their desired shape when the blood filter is properly deployed. Such materials include, but are not limited to, stainless steel, titanium and other metals. A particularly preferred material for the plurality of central struts in this regard is nickel-titanium, known to those in the art as Nitinol.

The present invention is intended to be used in the treatment of patients for pulmonary embolism by implantation into the venae cavae of a patient; however, the inventor also contemplates its use in other large veins of the patient to reduce a variety of circulatory occlusions such as those in patients suffering from deep vein thrombosis.

Figure 3:
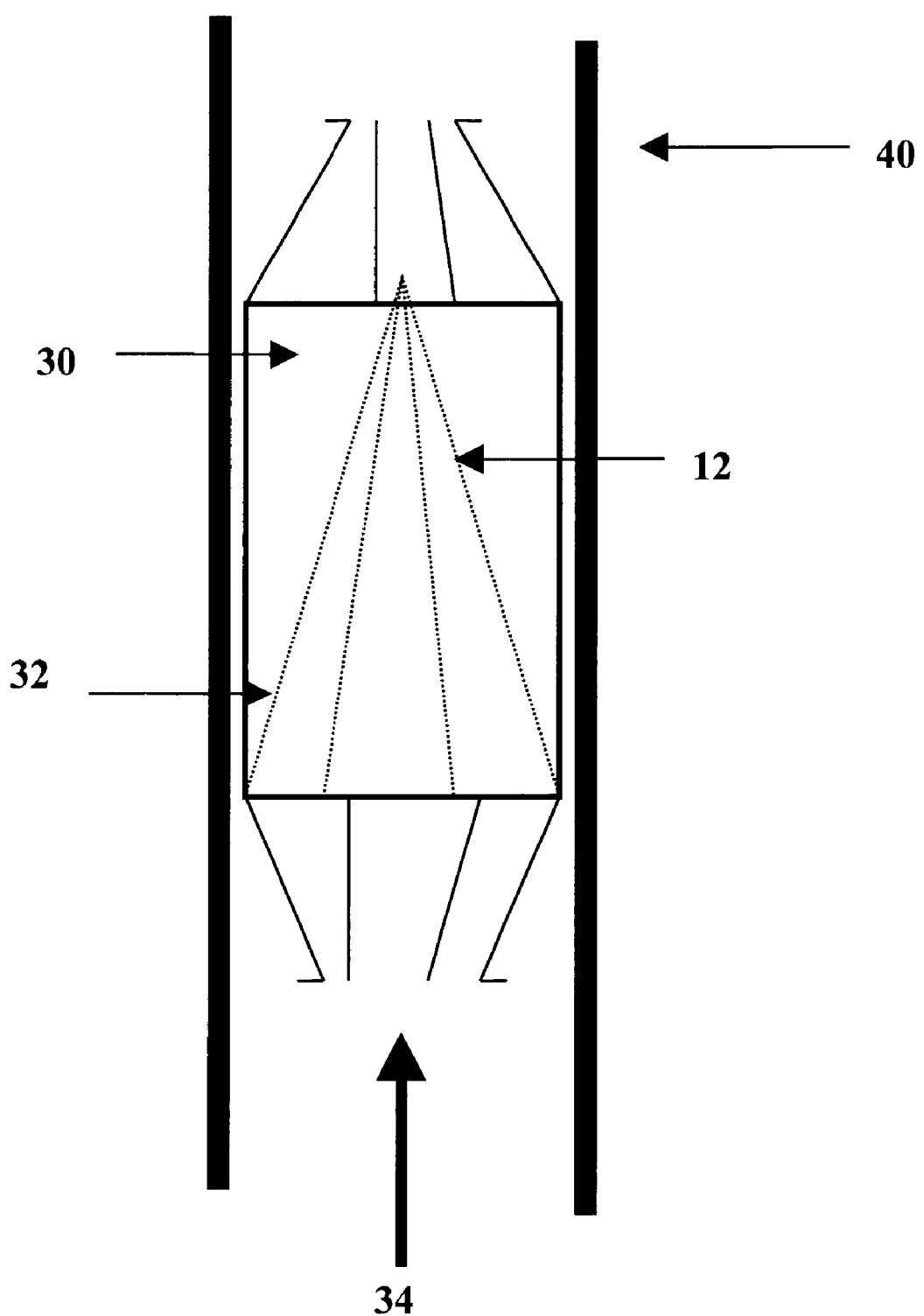
FIG. 3 illustrates the blood filter of the present invention properly emplaced within a blood vessel.

The procedure for using the blood filter of the present invention is as follows: the venous system of a patient is surgically accessed and the blood filter is positioned within the vessel, such as the vena cava, so that blood flows through the filter from the proximal end to the distal end of the filter. This positioning can be accomplished by using filter deployment techniques known to those in the art, preferably including the use of fluoroscopy to allow more accurate placement within the blood vessel. As depicted in FIG. 3, when the blood filter of the present invention 10 is properly emplaced, the hollow tubular member 14 lies adjacent to, and may even be in contact with, the blood vessel wall 40. The incision is closed and the blood flowing through the vessel passes through the filter, which traps emboli. If the blood vessel is a vena cava, the filtered blood returns directly to the right atrium of the heart.

Because the hollow tubular member 14 is made of a material that resists the ingrowth of tissue around the plurality of central struts, the blood filter of the present invention may remain within the blood vessel for a longer period of time than other filters, thus providing the patient with longer term protection from pulmonary embolism or other circulatory occlusions. Unlike permanent vena cava filters and other temporary vena cava filters, when there no longer is an indication for its continued use, the blood filter of the present invention may be easily removed with reduced concerns about complications arising from tissue ingrowth.

Figure 4:
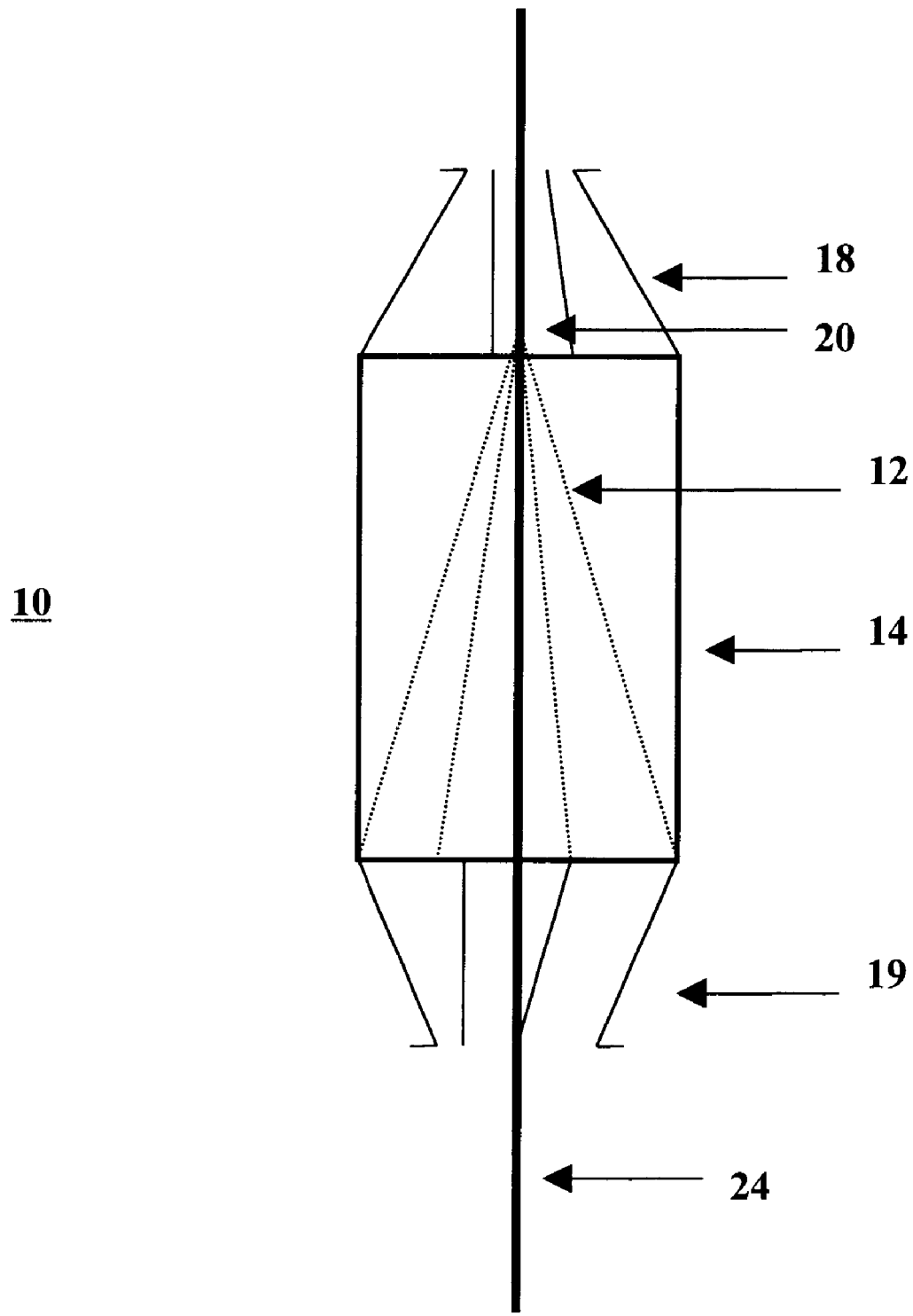
FIG. 4 illustrates the placement a guide wire through the blood filter of the present invention.
Figure 5:
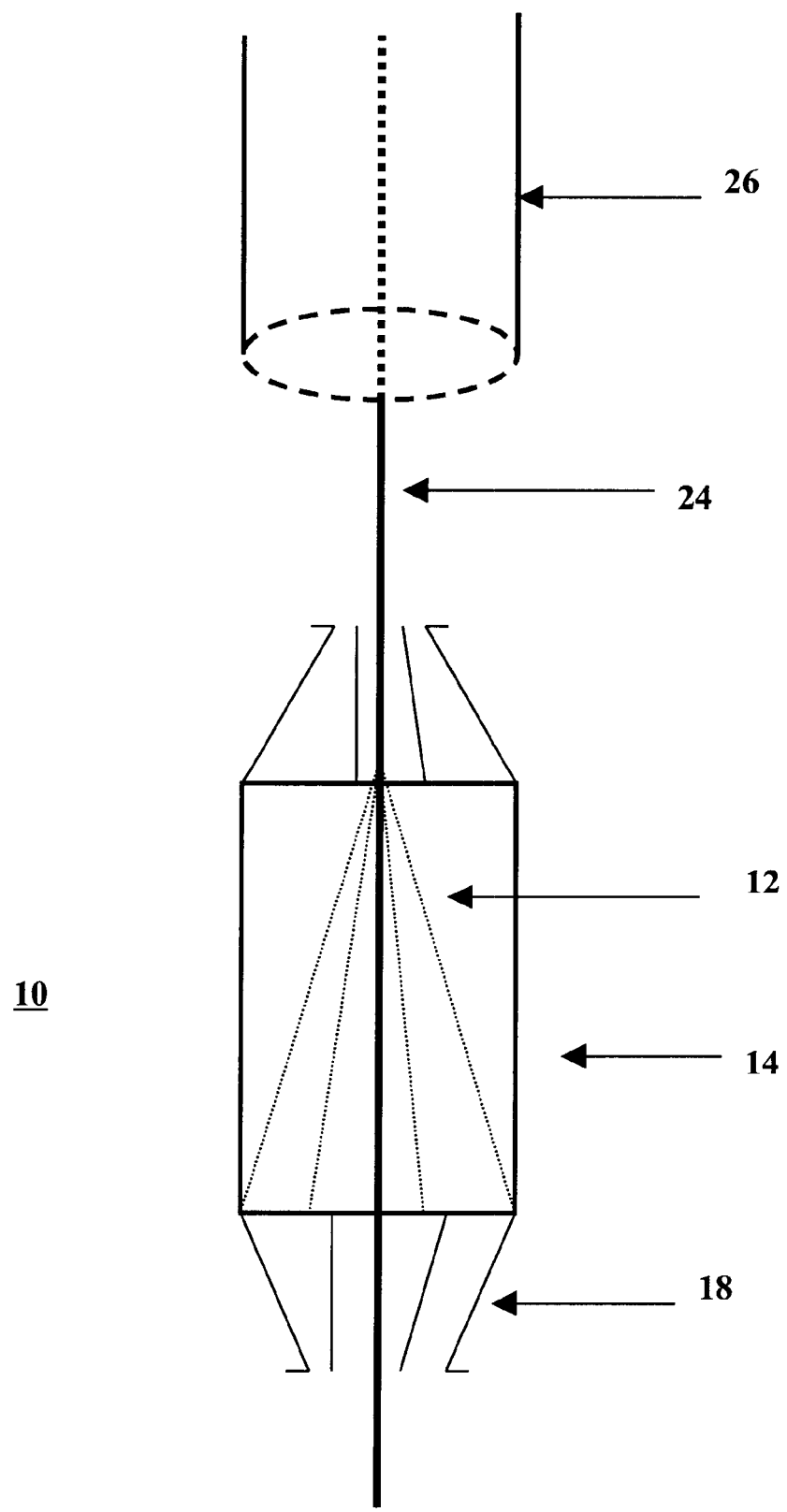
FIG. 5 illustrates the placement of a catheter over the blood filter of the present invention.
Figure 6:
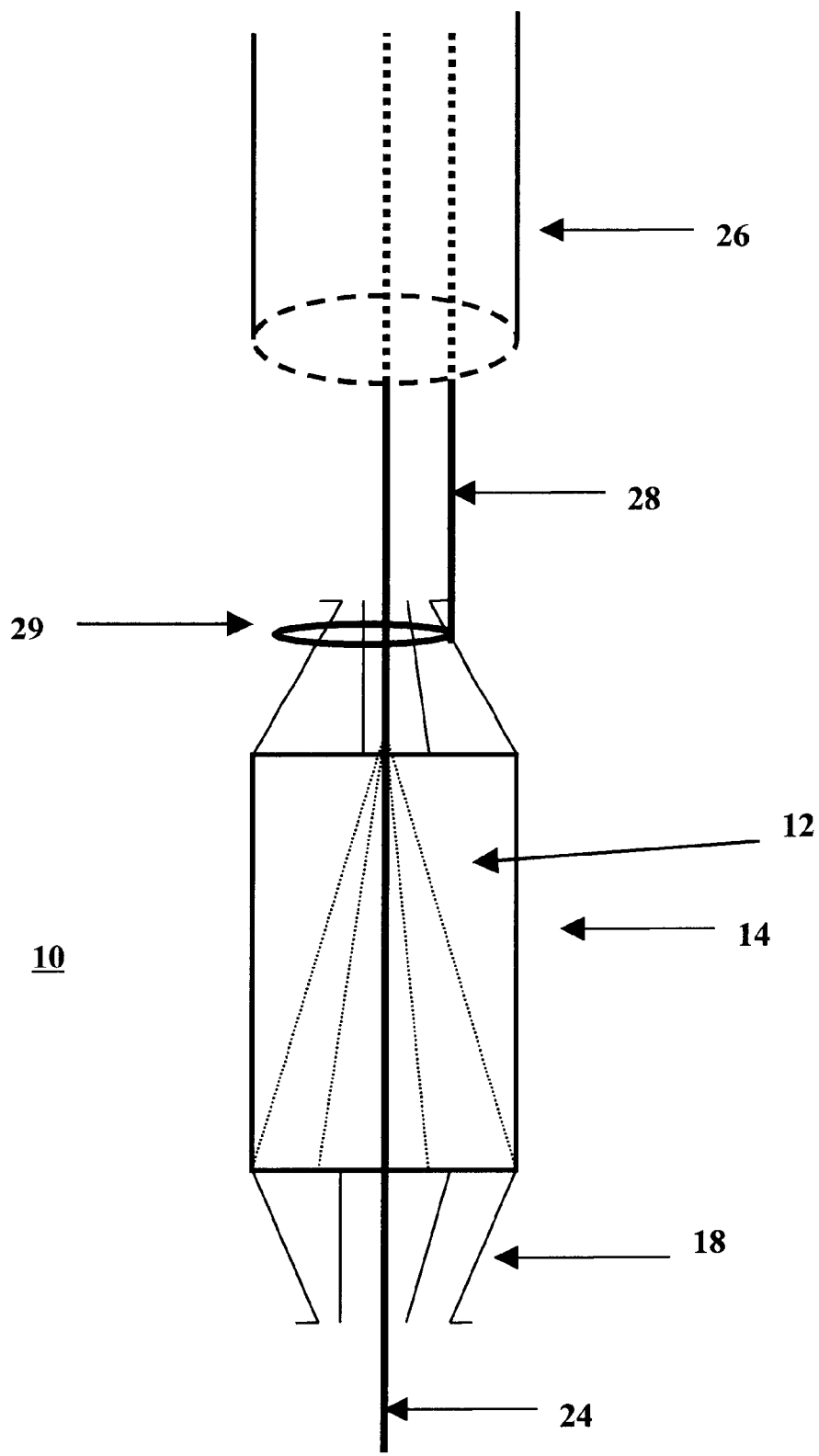
FIG. 6 illustrates the placement of a snare wire around the hooks of the vertical struts of the blood filter of the present invention.
Figure 7:
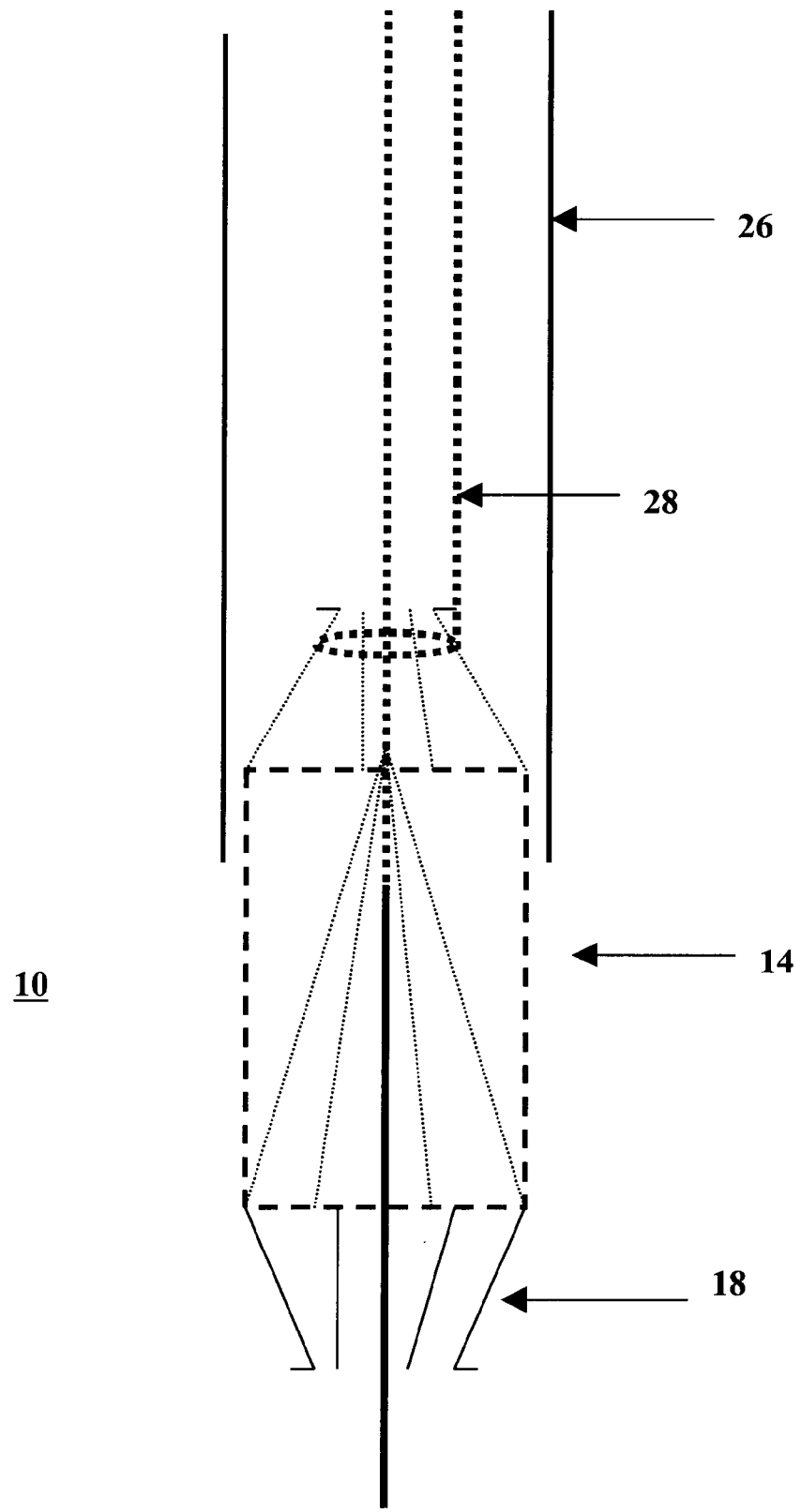
FIG. 7 illustrates the withdrawal of the blood filter of the present invention into a catheter.

A preferred procedure for removal of the blood filter of the present invention is illustrated in FIGS. 4–7. When use of the blood filter is no longer indicated, the venous system of the patient can again be surgically accessed and a guide wire 24 preferably can be placed through the central struts 12 of the blood filter 10 as shown in FIG. 4. A long catheter 26 can preferably be placed over the guide wire 24 as depicted in FIG. 5. A loop 29 of a snare wire 28 can preferably be placed around the guide wire 24 and through the catheter 26 as illustrated in FIG. 6. The loop 29 preferably encircles and engages the hooks 19 of the vertical struts 18. Although depicted herein as taking place at the distal end, the encircling and engaging by loop 29 can be performed at either end of the filter. The blood filter of the present invention can preferably be withdrawn into catheter 26, as illustrated in FIG. 7, and removed from the blood vessel.

Although the blood filter of the present invention has been described for use within venae cavae to treat pulmonary embolism, those skilled in the art will recognize its applicability in reducing other circulatory occlusions, such as those encountered by patients suffering from deep vein thrombosis, by filtering the blood in various large veins of the patient. Such large veins include, but are not limited to, jugular, femoral and iliac veins.

The inventor further contemplates that in some cases, blood filters of the present invention may be surgically implanted in more than one blood vessel of a patient to provide the patient with even greater protection from circulatory occlusions than would be provided by a single filter. Those filters may be removed when there is no longer an indication for their continued use. Because of the hollow tubular member of the blood filter of the present invention resisting tissue ingrowth around the struts of the filters, such a treatment option may be offered to patients. However, such a treatment likely could not be contemplated with other temporary filters because of concerns about complications arising from tissue ingrowth.

The foregoing illustrations of embodiments of the present invention are offered for the purposes of illustration and not limitation. It will be readily apparent to those skilled in the art that the embodiments described herein may be modified or revised in various ways without departing from the spirit and scope of the invention. The scope of the invention is to be measured by the appended claims.

I claim:

1. A blood filter comprising:
    a plurality of central struts, the distal ends thereof intersecting at a vertex;
    a hollow tubular member having distal and proximal ends in fluid communication, and having at least one vertical strut extending therefrom; and
    means for retaining said plurality of central struts within said hollow tubular member.

2. The blood filter of claim 1, wherein at least the outer layer of said hollow tubular member comprises a flexible, biocompatible, ingrowth-resistant material.

3. The blood filter of claim 2, wherein said flexible, biocompatible, ingrowth-resistant material is a member selected from the group consisting of polytetrafluoroethylene, low density polyethylene, high density polyethylene, polyesters made from polyethylene terephthalate, polypropylene, polystyrene, polycarbonate, fluorinated ethylene propylene and tetrafluoroethylene.

4. The blood filter of claim 2, wherein said flexible, biocompatible, ingrowth-resistant material comprises polytetrafluoroethylene.

5. The blood filter of claim 1, wherein said plurality of central struts are comprised of metal.

6. The blood filter of claim 1, wherein said plurality of central struts are made of a material selected from the group consisting of stainless steel, titanium and nickel-titanium.

7. The blood filter of claim 1, wherein said plurality of central struts are comprised of nickel-titanium.

8. The blood filter of claim 1, wherein said at least one vertical strut further includes at least one hook thereon.

9. The blood filter of claim 1, wherein said at least one vertical strut is comprised of metal.

10. The blood filter of claim 1, wherein said at least one vertical strut is made of a material selected from the group consisting of stainless steel, titanium and nickel-titanium.

11. The blood filter of claim 1, wherein said at least one vertical strut is comprised of stainless steel.

12. The blood filter of claim 1, wherein said means for retaining comprises said central struts exerting a self-expanding radial force on said hollow tubular member to provide friction between said plurality of central struts and said hollow tubular member.

13. The blood filter of claim 1, wherein said means for retaining comprises at least one appendage on the proximal end of said plurality of central struts engaging said hollow tubular member.

14. The blood filter of claim 1, wherein said means for retaining comprises a portion of said plurality of central struts being embedded within said hollow tubular member.

15. The blood filter of claim 1, wherein the shape of said plurality of central struts in an expanded state is a member selected from the group consisting of conical, basket and umbrella.

16. A blood filter comprising:
    a plurality of central struts, the distal ends thereof intersecting at a vertex; and
    a hollow tubular member having distal and proximal ends in fluid communication, with at least one vertical strut extending therefrom,
        wherein said plurality of central struts are retained within said hollow tubular member.

17. The blood filter of claim 16, wherein at least the outer layer of said hollow tubular member comprises a flexible, biocompatible, ingrowth-resistant material.

18. The blood filter of claim 17, wherein said flexible, biocompatible, ingrowth-resistant material is a member selected from the group consisting of polytetrafluoroethylene, low density polyethylene, high density polyethylene, polyesters made from polyethylene terephthalate, polypropylene, polystyrene, polycarbonate, fluorinated ethylene propylene and tetrafluoroethylene.

19. The blood filter of claim 17, wherein said flexible, biocompatible, ingrowth-resistant material comprises polytetrafluoroethylene.

20. The blood filter of claim 16, wherein said plurality of central struts are comprised of metal.

21. The blood filter of claim 16, wherein said plurality of central struts are made of a material selected from the group consisting of stainless steel, titanium and nickel-titanium.

22. The blood filter of claim 16, wherein said plurality of central struts are comprised of nickel-titanium.

23. The blood filter of claim 16, wherein said at least one vertical strut further includes at least one hook thereon.

24. The blood filter of claim 16, wherein said at least one vertical strut is comprised of metal.

25. The blood filter of claim 16, wherein said at least one vertical strut is made of a material selected from the group consisting of stainless steel, titanium and nickel-titanium.

26. The blood filter of claim 16, wherein said at least one vertical strut is comprised of stainless steel.

27. The blood filter of claim 16, wherein the shape of said plurality of central struts in an expanded state is a member selected from conical, basket and umbrella.

28. A method of using a blood filter to reduce circulatory occlusion in a patient, said blood filter comprising a plurality of central struts, the distal ends thereof intersecting at a vertex and a hollow tubular member having distal and proximal ends in fluid communication, with at least one vertical strut extending therefrom, wherein said plurality of central struts are retained within said hollow tubular member, said method comprising:

surgically implanting said blood filter into a blood vessel of the patient such that said hollow tubular member lies adjacent to the inner wall of said blood vessel and such that blood flows through said filter.

29. The method of claim 28, wherein said blood vessel is a member selected from the group consisting of venae cavae, jugular vein, femoral vein and iliac veins.

30. The method of claim 28, wherein said blood vessel is the inferior vena cava.

31. The method of claim 28, wherein said blood vessel is the superior vena cava.

32. The method of claim 28 further including the step of surgically removing said blood filter.

33. The method of claim 28, wherein said circulatory occlusion comprises pulmonary embolism.

34. The method of claim 28, wherein said circulatory occlusion comprises deep vein thrombosis.

35. A method of using a blood filter to reduce circulatory occlusion in a patient, said blood filter comprising a plurality of central struts, the distal ends thereof intersecting at a vertex, a hollow tubular member having distal and proximal ends in fluid communication, and having at least one vertical strut extending therefrom, and means for retaining said plurality of central struts within said hollow tubular member, said method comprising:

surgically implanting said blood filter into a blood vessel of the patient such that said hollow tubular member lies adjacent to the inner wall of said blood vessel and such that blood flows through said filter.

36. The method of claim 35, wherein said blood vessel is a member selected from the group consisting of venae cavae, jugular vein, femoral vein and iliac veins.

37. The method of claim 35, wherein said blood vessel is the inferior vena cava.

38. The method of claim 35, wherein said blood vessel is the superior vena cava.

39. The method of claim 35 further including the step of surgically removing said blood filter.

40. The method of claim 35, wherein said circulatory occlusion comprises pulmonary embolism.

41. The method of claim 35, wherein said circulatory occlusion comprises deep vein thrombosis.

42. A method of using at least one blood filter to reduce circulatory occlusion in a patient, said at least one blood filter comprising a plurality of central struts, the distal ends thereof intersecting at a vertex, a hollow tubular member having distal and proximal ends in fluid communication with at least one vertical strut extending therefrom, and a means for retaining said plurality of central struts within said hollow tubular member, said method comprising:

surgically implanting at least one blood filter into at least one blood vessel of the patient such that blood flows through said at least one blood filter and such that said hollow tubular member lies adjacent to the wall of said at least one blood vessel.

43. The method of claim 42, wherein said at least one blood vessel is a member selected from the group consisting of venae cavae, jugular, femoral and iliac veins.

44. The method of claim 42, wherein said at least one blood vessel comprises the inferior vena cava.

45. The method of claim 42, wherein said at least one blood vessel comprises the superior vena cava.

46. The method of claim 42, wherein said circulatory occlusion comprises pulmonary embolism.

47. The method of claim 42, wherein said circulatory occlusion comprises deep vein thrombosis.

48. The method of claim 42 further including the step of surgically removing said at least one blood filter from said at least one blood vessel.

* * * * *